US011759650B2

(12) United States Patent
Arendash et al.

(10) Patent No.: US 11,759,650 B2
(45) Date of Patent: Sep. 19, 2023

(54) IMMUNOREGULATION, BRAIN DETOXIFICATION, AND COGNITIVE PROTECTION BY ELECTROMAGNETIC TREATMENT

(71) Applicant: NeuroEM Therapeutics, Inc., Phoenix, AZ (US)

(72) Inventors: Gary W. Arendash, Phoenix, AZ (US); Robert Baranowski, Escondido, CA (US)

(73) Assignee: NeuroEM Therapeutics, Inc., Tampa Bay, FL (US)

( * ) Notice: Subject to any disclaimer, the term of this patent is extended or adjusted under 35 U.S.C. 154(b) by 328 days.

(21) Appl. No.: 16/865,250

(22) Filed: May 1, 2020

(65) Prior Publication Data

US 2020/0261737 A1   Aug. 20, 2020

Related U.S. Application Data

(63) Continuation-in-part of application No. 16/359,749, filed on Mar. 20, 2019, and a continuation-in-part of
(Continued)

(51) Int. Cl.
*A61N 2/00* (2006.01)
*A61N 2/02* (2006.01)
(Continued)

(52) U.S. Cl.
CPC ............ *A61N 2/004* (2013.01); *A61N 1/0476* (2013.01); *A61N 1/36025* (2013.01); *A61N 1/40* (2013.01);
(Continued)

(58) Field of Classification Search
CPC .. A61N 2/004; A61N 1/0476; A61N 1/36025; A61N 1/40; A61N 2/02; A61N 5/0624; A61N 2005/0647
See application file for complete search history.

(56) References Cited

U.S. PATENT DOCUMENTS

| 6,248,126 | B1 | 6/2001 | Lesser |
| 6,334,069 | B1 | 12/2001 | George |

(Continued)

FOREIGN PATENT DOCUMENTS

| EP | 1907052 | 1/2010 |
| EP | 1606010 B1 | 2/2012 |

(Continued)

OTHER PUBLICATIONS

"Loop Antenna" Wikipedia website print date Dec. 6, 2022.*
(Continued)

*Primary Examiner* — Mark W. Bockelman
(74) *Attorney, Agent, or Firm* — Nathan G. Guymon; Bamert Regan PLLC

(57) ABSTRACT

In one example in accordance with the present disclosure a method of normalizing cytokine levels in a blood stream of a subject is described. According to the method, an array of electromagnetic emitters is positioned proximal to the subject. An electromagnetic wave generator generates electromagnetic fields having a predetermined frequency. Cytokine levels are normalized in the blood stream of the subject by applying the electromagnetic fields to the subject through the electromagnetic emitters.

26 Claims, 14 Drawing Sheets

Related U.S. Application Data application No. 16/273,519, filed on Feb. 12, 2019, and a continuation-in-part of application No. 14/205,333, filed on Mar. 11, 2014, now Pat. No. 10,765,879.

(60) Provisional application No. 61/776,097, filed on Mar. 11, 2013.

(51) Int. Cl.
*A61N 5/06* (2006.01)
*A61N 1/04* (2006.01)
*A61N 1/40* (2006.01)
*A61N 1/36* (2006.01)

(52) U.S. Cl.
CPC ............. *A61N 2/02* (2013.01); *A61N 5/0624* (2013.01); *A61N 2005/0647* (2013.01)

(56) References Cited

U.S. PATENT DOCUMENTS

| | | |
|---|---|---|
| 6,410,137 B1 | 6/2002 | Bunyan |
| 6,463,336 B1 | 10/2002 | Mawhinney |
| 6,876,337 B2 | 4/2005 | Larry |
| 7,672,648 B1 | 3/2010 | Groe |
| 8,684,901 B1 | 4/2014 | Zabara |
| 8,868,177 B2 | 10/2014 | Simon et al. |
| 9,672,393 B1 | 6/2017 | Zhu |
| 10,765,879 B2 * | 9/2020 | Arendash ................. A61N 1/40 |
| 10,792,483 B2 | 10/2020 | Andocs |
| 10,850,096 B2 | 12/2020 | Teng |
| 11,058,886 B1 | 7/2021 | Matloubian |
| 11,229,788 B1 | 1/2022 | John |
| 2004/0122281 A1 | 6/2004 | Fischell |
| 2004/0127895 A1 | 7/2004 | Flock |
| 2004/0176805 A1 | 9/2004 | Whelan |
| 2004/0181115 A1 | 9/2004 | Sandyk et al. |
| 2004/0199070 A1 | 10/2004 | Krockel |
| 2005/0228209 A1 | 10/2005 | Schneider |
| 2007/0244530 A1 | 10/2007 | Ren |
| 2008/0269851 A1 | 10/2008 | Deem |
| 2009/0131739 A1 | 5/2009 | Shalev |
| 2009/0156884 A1 | 6/2009 | Schneider |
| 2009/0276019 A1 | 11/2009 | Perez |
| 2009/0326315 A1 * | 12/2009 | Nishi ....................... A61N 2/02 600/14 |
| 2010/0042168 A1 | 2/2010 | Pasche et al. |
| 2010/0114086 A1 | 5/2010 | Deem et al. |
| 2010/0210894 A1 | 8/2010 | Pascual-Leone |
| 2011/0230701 A1 | 9/2011 | Simon et al. |
| 2012/0065456 A1 | 3/2012 | Arendash et al. |
| 2012/0089201 A1 | 4/2012 | Pilla |
| 2012/0172954 A1 | 7/2012 | Zastrow |
| 2012/0289869 A1 | 11/2012 | Tyler |
| 2013/0237742 A1 | 9/2013 | Capstick |
| 2014/0187851 A1 | 7/2014 | Cetroni |
| 2014/0228620 A1 | 8/2014 | Vasishta |
| 2014/0257017 A1 * | 9/2014 | Arendash ................. A61N 1/40 600/13 |
| 2014/0303425 A1 | 10/2014 | Pilla |
| 2014/0330353 A1 | 11/2014 | Knight |
| 2015/0209566 A1 | 7/2015 | Peyman |
| 2015/0342661 A1 | 12/2015 | Ron Edoute |
| 2016/0022976 A1 | 1/2016 | Peyman |
| 2017/0014637 A1 | 1/2017 | Basser |
| 2017/0065326 A1 | 3/2017 | Rosen |
| 2017/0209579 A1 | 7/2017 | Curley |
| 2019/0030354 A1 | 1/2019 | Turner |
| 2019/0290355 A1 | 9/2019 | Amos |
| 2020/0038509 A1 | 2/2020 | Corr |
| 2020/0078600 A1 | 3/2020 | Dinh |
| 2020/0164195 A1 | 5/2020 | Lowsky |
| 2020/0297286 A1 | 9/2020 | Costa |
| 2020/0346028 A1 | 11/2020 | Arendash et al. |
| 2020/0360709 A1 * | 11/2020 | Luttrull .................. A61N 1/403 |
| 2021/0153925 A1 | 5/2021 | Kim |
| 2021/0177491 A1 | 6/2021 | Onik |
| 2021/0220480 A1 | 7/2021 | Peyman |
| 2021/0338265 A1 | 11/2021 | Cohn |

FOREIGN PATENT DOCUMENTS

| | | |
|---|---|---|
| EP | 2414038 | 2/2012 |
| WO | WO-2007044386 | 4/2007 |
| WO | 2008008545 A3 | 9/2008 |
| WO | WO-2008141296 | 11/2008 |
| WO | 2017157874 A1 | 9/2017 |
| WO | 2020102312 A1 | 5/2020 |
| WO | 2020141527 A1 | 7/2020 |
| WO | 2020180653 A1 | 9/2020 |

OTHER PUBLICATIONS

"Transcranial Electromagnetic Treatment Against Alzeheimer's Disease: Why it has the Potential to Trump Alzheimer Disease Drug Development" Journal of Alzheimer;'s Diseasr.* https://neuroem.com/our-technology/—print date 12.*

Gary W. Arendash, "Transcranial Electromagnetic Treatment Against Alzheimber's Disease: Why it has the Potential to Trump Alzheimer's Disease Drug Development," Journal of Alzheimer's Disease, 32 (Jun. 2012) pp. 243-266.

Nguyen, et al; "The Effect of a High Frequency Electromagnetic Field in the Microwave Range on Red Blood Cells"; Sep. 7, 2017.

Karsten, et al; "Red Blood Cells are Dynamic Reservoirs of Cytokines"; Feb. 15, 2018.

Rasouli; "Attenuation of interleukin-1beta by pulsed electromagnetic fields after traumatic brain injury"; Neuroscience Letters 519 (2012) 4-8.

Merighi; "Signaling pathways involved in anti-inflammatory effects of Pulsed Electromagnetic Field in microglial cells"; Cytokine 125 (2020) 154777.

Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.

Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.

Gerstner Elizabeth R. et al., AntiEndothelial Growth Factor Therapy for Malignant Glioma, Curr Neurol Neurosci Rep. May 2009, 9(3):254-262, p. 2, paragraphs 2-3.

* cited by examiner

IMMUNOREGULATION, BRAIN DETOXIFICATION, AND COGNITIVE PROTECTION BY ELECTROMAGNETIC TREATMENT

RELATED APPLICATIONS

The present application claims benefit to and is a continuation-in-part of U.S. application Ser. No. 14/205,333, filed Mar. 11, 2014, which claims the benefit of U.S. Provisional Application No. 61/776,097, filed Mar. 11, 2013. The present application also claims benefit to and is a continuation-in-part of U.S. application Ser. No. 16/273,519, filed Feb. 12, 2019. The present application also claims benefit to and is a continuation-in-part of U.S. application Ser. No. 16/359,749, filed Mar. 20, 2019. These applications are incorporated herein by reference in their entireties.

BACKGROUND OF INVENTION

There are a number of human diseases/infections wherein dysregulation of the body's immune system occurs. This immune dysfunction or dysregulation can be a significant component to the disease/infection process and symptoms, or a primary response of the body to the disease/infection. Moreover, immune dysfunction associated with various diseases/infections can affect not only peripheral tissues (e.g., rheumatoid arthritis, COVID-19, asthma), but can also affect the brain (e.g., Alzheimer's Disease, Multiple Sclerosis, Postoperative Cognitive Dysfunction). Regarding immune dysregulation in the human brain, blood flowing through the brain's dense vascular system contains white blood cells (WBCs) that secrete a variety of cytokines—the immune system's "modulators" or "effectors." As well, the brain parenchyma's microglia and astrocytes secrete cytokines that influence brain function.

Meningeal lymphatic vessels on the human brain's surface, and lymphocytes within these vessels, indicate a direct linkage between the immune system and brain function/dysfunction. These meningeal lymphatic vessels drain toxic substances, such as aggregated β-amyloid (Aβ) and tau, from the brain.

As a neurodegenerative brain disease involving dysfunction of the immune system, Alzheimer's Disease (AD) tragically affects six million Americans, with another five million Americans having the prelude to AD called Mild Cognitive Impairment (MCI). When considered globally, AD effects 10s, if not 100s of millions of lives. There is currently no way to reverse, stop, or even slow down the progressive cognitive deterioration of AD. It is the 6th leading cause of death in the U.S., and at a cost to the U.S. government of over $200B every year, AD has the potential to compromise the U.S. healthcare system by 2050 if an effective treatment or preventative is not found. Despite billions of dollars spent trying to find a drug or biologic to treat AD, clinical trials involving over 150 drugs or biologics to treat or prevent the disease have thus far been disappointing.

Consequently, "non-pharmacologic" approaches against the disease have emerged and have been clinically tested, or are currently being clinically tested, in AD subjects. These neuromodulatory approaches include transcranial magnetic stimulation (tMS), transcranial direct current stimulation (tDCS), and deep brain stimulation (DBS). All three of these approaches stimulate the activity of neurons in the brain. However, as is the case for pharmaceutic and biological agents, none of these approaches have thus far been shown to improve the cognitive function of AD subjects or affect the AD process. Two newer neuromodulatory approaches (transcranial photomodulation and transcranial ultrasound treatment) are only now beginning clinical trials against AD. Collectively, these five neuromodulatory approaches have not been shown to address the immune dysfunction in AD, particularly as defined by abnormal blood levels of both inflammatory and non-inflammatory cytokines.

BRIEF DESCRIPTION OF THE DRAWINGS

The accompanying drawings illustrate various examples of the principles described herein and are a part of the specification. The illustrated examples do not limit the scope of the claims.

Figure 1:
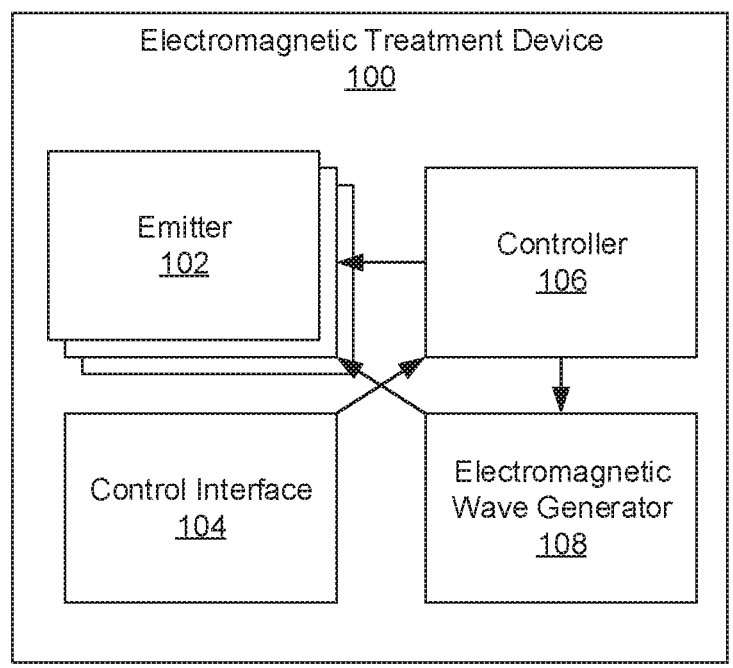
FIG. 1 is a block diagram of an electromagnetic treatment device, according to an example of the principles described herein.

The presented figures provide examples and/or implementations consistent with the methods described in this provisional application. However, the description is not limited to the examples and/or implementations shown in the figures.

DETAILED DESCRIPTION OF THE INVENTION

Although there is a general consensus among AD researchers that the immune system plays an important role in AD pathogenesis, there is disagreement as to whether progression of AD involves an over-activation (high blood cytokine levels) or an under-activation (low blood cytokine levels) of the immune system. Some AD researchers believe that AD, at least in part, is caused by brain inflammation (neuroinflammation) and that administration of agents that lower the high cytokine levels in the brain's vasculature could be therapeutic. Others believe that AD can involve a "hypoactive" immune system and, as such, the subject's low cytokine levels make them susceptible to AD. Under this scenario, AD subjects with a hypoactive immune system would require a therapeutic that activates (increases) cytokine secretion by WBCs.

In either over-activated or under-activated cases, the immune system's cytokine levels in blood are abnormal. Accordingly, the present specification presents systems and methods that address the immune (cytokine) dysfunction of AD, as well as the immune imbalance of a host of other peripheral and brain diseases wherein immune(cytokine)-dysregulation is central to their pathogenesis. A method that could regulate/modulate blood cytokines such that they return to normal or near normal levels in these conditions could result in significant improvement in disease symptoms and possibly arrest or reverse disease progression.

Transcranial electromagnetic treatment (TEMT) is a promising neuromodulatory approach against AD. Comprehensive pre-clinical studies in AD transgenic mice have shown that TEMT penetrates the brain and its neurons to "disaggregate" small intra-neuronal aggregates/oligomers of two toxic proteins that appear to be the root causes of AD-Aβ and tau. These actions by TEMT, in combination with its ability to enhance mitochondrial function in neurons, appear to play a role in the consistent cognitive benefits provided by TEMT in AD transgenic mice.

To translate these findings to clinical trials in human AD subjects, the MEMOREM™ device provides full forebrain treatment with electromagnetic waves through multiple emitters distributed on the human head surface to induce electromagnetic fields in the brain. As an example of a device that provides EM fields into the brain, the MEMOREM™ device has been shown to provide considerable cognitive benefit to AD subjects, changes in their Aβ levels within cerebrospinal fluid (CSF) consistent with Aβ disaggregation in the brain, and evidence of enhanced brain function in their functional magnetic resonance imaging (fMRI) scans. Thus, devices such as the MEMOREM™ device that provide electromagnetic field treatment to the brain could provide significant therapeutic benefits. The present specification describes a variety of ways of applying electromagnetic field treatment to benefit the human brain and body in different ways. The content of the present specification were arrived at from "human" studies (not in vitro or animal studies), and, as such, should have direct applicability to humans.

Accordingly, the present specification presents methods to 1) provide immunoregulation in both the human body and brain, as defined by the lowering of high cytokine levels and/or the increasing of low cytokine levels in the blood, 2) increase clearance of toxins from the brain through enhancement of brain lymphatic drainage, 3) regulate blood markers of AD in the same direction as its ability to regulate blood cytokines, 4) protect against or treat cognitive impairment that results from being on a ventilator and/or high oxygen for an extended time, and 5) protect against post-surgical cognitive dysfunction or cognitive impairment/brain fog following surgery under anesthesia.

The present specification describes two methodologies that can address a variety of conditions to improve normal human health. Specifically, a first method is provided whereby the human brain is treated with electromagnetic fields through transcranial electromagnetic treatment or TEMT. A second method provides electromagnetic fields to the body or periphery through peripheral electromagnetic treatment or PEMT. The use of these two bioengineering methodologies for each of multiple health areas is described in the present specification.

These areas range from immunoregulation, to clearance of toxic proteins from the brain, to changes in blood cytokines associated with changes in AD markers, to resolving immune and cognitive complications resulting from viral/bacterial infections and surgery with anesthesia. The methods described in the present specification provide such immunoregulation, enhance clearance of toxic proteins from the brain, induce parallel changes in blood immune and AD markers, and alleviate both immune and cognitive complications that can result from viral/bacterial infections and surgery with anesthesia. Therefore, the TEMT and PEMT methodologies of the present specification provide beneficial effects to humans, and may result in their return to a healthy condition.

Turning now to the figures, FIG. 1 is a block diagram of an electromagnetic treatment device (100), according to an example of the principles described herein. Specifically, FIG. 1 depicts an electromagnetic treatment device (100) that includes an array of electromagnetic emitters (102). The electromagnetic emitters (102) may be positioned adjacent a head surface of the subject in, for example, a transcranial electromagnetic treatment (TEMT) device (100). In another example, the electromagnetic emitters (102) are positioned adjacent a body surface of the subject in, for example, a peripheral electromagnetic treatment (PEMT). The electromagnetic emitters (102) project an electromagnetic frequency field toward the head and/or body of the patient. The electromagnetic emitter(s) (102) is (are) activated to apply electromagnetic fields/treatment to the patient primarily for the remedy of diseases or conditions of immune system dysregulation wherein blood cytokine levels are abnormally high or low, although other potentially beneficial actions are induced.

In one example, electromagnetic waves may be generated by the electromagnetic wave generator (108), sent to an emitter (102) and then passed into tissue as an electromagnetic field. The electromagnetic treatment device (100) may include a control interface (104), a controller (106), an electromagnetic wave generator (108), and one or more electromagnetic emitters (102) that apply the treatment to the desired portion of the brain or body.

The controller (106) manages the treatment and its parameters by manipulating the electromagnetic wave generator (108) and electromagnetic emitters (102) as per the prescribed treatment. The control interface (104) allows a patient or a caregiver to start/stop treatments and to view treatment status. The electromagnetic treatment device (100) may be portable so that treatment can be applied while a patient is moving around or could be fixed, allowing a patient to receive treatment when positioned correctly relative to the electromagnetic treatment device (100). Electromagnetic emitters (102) may be activated one at a time by the controller (106), or several electromagnetic emitters (102) may be activated to produce electromagnetic (e.g., radio frequency) field combinations that are summed to produce controllable patterns where desired on the patient.

As will be described below in more detail, the electromagnetic treatment device (100) provides: 1) immunoregulatory/immunomodulatory actions to lower or raise blood cytokine levels toward a norm, 2) removal of toxic substances from the brain by enhancing their brain clearance, 3) the ability to modulate Alzheimer's markers in the blood in the same direction as the method's ability to modulate blood cytokine levels, 4) the ability to protect against or treat cognitive impairment that can result from being on a ventilator and/or higher than normal oxygen for an extended period, and 5) reduction or elimination of post-operative cognitive dysfunction/brain fog or cognitive impairment following surgery under anesthesia.

Figure 2:
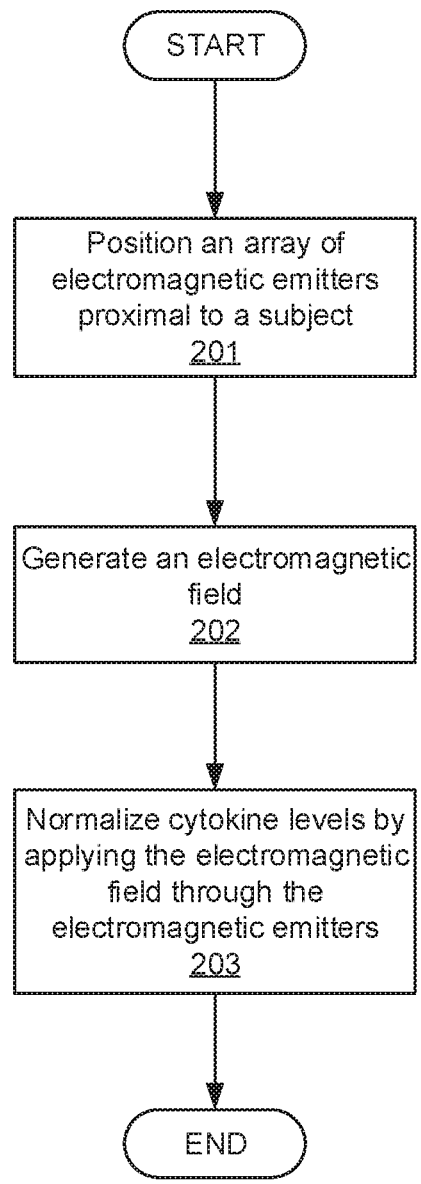
FIG. 2 is a flowchart of a method for normalizing cytokine levels in a blood stream of a subject, according to an example of the principles described herein.

FIG. 2 is a flowchart of a method (200) for normalizing cytokine levels in a blood stream of a subject, according to an example of the principles described herein. According to the method (200), an array of electromagnetic emitters (FIG. 1, 102) are positioned (block 201) proximal to the subject. As described above, such placement may be adjacent to a head surface or adjacent to a body surface of the subject.

The electromagnetic wave generator (FIG. 1, 108) then generates (block 202) an electromagnetic field. In some examples, the waves of the field have a frequency between 1 megahertz (MHz) and 430 GHz (gigahertz), a power level between 0.1 and 8 watts per kilogram (W/kg) average specific absorption rate (SAR), and a pulse repetition rate between 1 and 300 hertz.

The method (200) also includes normalizing (block 203) cytokine levels by applying electromagnetic fields to the subject through the electromagnetic emitters (FIG. 1, 102). In a particular example, cytokine levels are normalized in blood vessels, lymphatic vessels, and brain tissue beneath the emitters. In some examples, a treatment session may have a specified duration of for example a few minutes, to a few hours. This treatment session may be repeated at predetermined intervals, for example for multiple times a day, for multiple times a week, etc. over a longer period of time such as a month or even years. In other examples, treatment may be continuous over days, weeks, months, or years.

A large number of diseases/conditions involve a dysfunction/imbalance of the immune system—specifically, as defined as a dysfunction/imbalance in blood levels of various cytokines. In some of these diseases/conditions, the immune system is "hyperactive", with higher than normal blood levels of cytokines being present. In this example, normalizing (block 203) cytokine levels includes decreasing cytokine levels. Diseases/conditions wherein a hyperactive immune system is apparently involved in the disease/condition include Alzheimer's Disease, bacterial or viral infections (e.g., COVID-19, Ebola, SARS, certain influenzas), Rheumatoid Arthritis, Multiple Sclerosis, Parkinsons' Disease, arterial hypertension, autoimmune diseases, psoriasis, cognitive impairment in depression, allergy, asthma, coeliac disease, glomerulonephritis, hepatitis, inflammatory bowel disease, Crohn's disease, osteoarthritis, fibromyalgia, cardiovascular diseases (e.g., atherosclerosis), cancer, diabetes, chronic obstructive pulmonary disease (COPD), chronic kidney disease, systemic lupus erythematosus, and metabolic syndrome.

Other diseases/conditions have a hypoactive immune system involving low blood levels of cytokines. In this example, the normalizing (block 203) cytokine levels includes increasing cytokine levels. These diseases/conditions include Alzheimer's Disease (unresolved whether hypo- or hyperactive immune system is involved), AIDS, Traumatic Brain Injury (TBI), and chronic widespread pain.

Regarding Alzheimer's Disease (AD), it may be the case that the disease involves uncontrolled brain inflammation (neuroinflammation) or systemic inflammation, which may be responsible for at least some of the disease progression from mild cognitive impairment (MCI) to the various stages of AD. However, the opposite may be the case,—namely, that the brain and/or body immune system is hypoactive and that the resulting inability to resist AD pathogenesis plays a role in the conversion of MCI to AD, with progressive cognitive impairment continuing thereafter due to a hypoactive immune system. In either case, the present method (200) regulates blood cytokine levels toward their normal blood levels, which may include reducing brain inflammation in AD or up-regulating cytokine levels to resist this disease. Such a method (200) could even beneficially increase cytokine levels above normal and may also be therapeutic against the multitude of diseases/conditions involving immune dysregulation listed above.

In view of the above, the present specification describes a method (200) for providing "electromagnetic fields/treatment" to the brain (TEMT) or body (PEMT), which would result in an immunoregulatory function of treatment on circulating blood in the brain or body by increasing blood cytokine levels if they are too low or decreasing blood cytokine levels if they are too high.

As a summary, in a first example of addressing an imbalance in blood levels of various cytokines, the method (200) includes using an electromagnetic treatment device (FIG. 1, 100) employing an electromagnetic wave generator (FIG. 1, 108), and cable-connected radiating emitters (FIG. 1, 102) on the head to generate and radiate electromagnetic field treatment across the cranium and into the brain of a patient. The electromagnetic treatment device (FIG. 1, 100) provides in-home electromagnetic wave treatment while allowing for near complete mobility. Such an electromagnetic treatment device (FIG. 1, 100) may include a custom-printed circuit board (controller (FIG. 1, 106)) powered by a rechargeable battery. The electromagnetic treatment device (FIG. 1, 100) in one example provides full forebrain TEMT through its constellation of eight specialized electromagnetic emitters (FIG. 1, 102) embedded within a double-layered head cap. In this example, these electromagnetic emitters (FIG. 1, 102) may be activated sequentially, with only one electromagnetic emitter (FIG. 1, 102) active at any given time. When an electromagnetic emitter (FIG. 1, 102) is active, it projects electromagnetic fields into the brain. For this example, computer simulations indicate that electromagnetic fields easily penetrate through the cranium, then the underlying cerebral cortex, and finally into deep sub-cortical brain areas. For treatment purposes, electromagnetic fields are defined as consisting of electromagnetic waves received by an electromagnetic emitter (FIG. 1, 102), that then propagates electromagnetic fields through the air and that then penetrate some degree into the body of the patient receiving treatment.

The electromagnetic device (FIG. 1, 100) described above provides electromagnetic treatment not only to neurons and glial cells that make up the cellular part of the brain, but also to cerebral vessels on the surface of the brain and deep cerebral vessels located within or below the cerebral cortex. That is, the area under the electromagnetic emitters (FIG. 1, 102) includes the brain's neurons, glial cells and cerebral vessels. As such, the cellular components of blood circulating through those cerebral vessels (particularly lymphocytes) could be affected by electromagnetic fields emanating from electromagnetic emitters (FIG. 1, 102) positioned on the head's surface.

In a clinical study that administered TEMT through such a TEMT device to mild/moderate AD subjects, blood samples were taken at baseline, after the first 1-hour treatment, and after 60 days of twice-daily 1-hour treatments. Analysis of plasma fora panel of eight cytokines (GCSF, GMCSF, PDGF, VEGF, IL-10, IL-15, IL-17A, and IL-18) revealed a clear immunoregulatory ability of TEMT. Specifically, if baseline cytokine levels were low (below normal), 60 days of TEMT resulted in elevated cytokine levels, usually at least to normal levels. Conversely, if blood cytokine levels were high (above normal), TEMT induced a reduction, usually near, or to, normal levels. These results have profound implications since diseases/conditions characterized by a hypo-active immune system could be reactivated by TEMT such that, in the case of AD, the reactivated immune system could prevent or resist AD pathogenesis. A similar, but opposite scenario, can be envisioned for diseases/conditions characterized by a hyper-active immune system.

In the same clinical study, analysis of cytokine levels after only one hour of TEMT revealed treatment changes already occurring in the same direction as those seen after 60 days of treatment. Baseline cytokines levels (below or above normal) were universally predictive of their treatment response—always toward normal levels for all subjects and all cytokines even after this one treatment. Activation or suppression of Treg cells by TEMT may be one possible explanation for this rapid cytokine response to TEMT. It is assumed that such profound immunoregulatory ability of electromagnetic fields would also be evident in individuals with or without diseases/conditions involving immune dysfunction.

As a more specific example of addressing imbalance in blood levels of various cytokines, TEMT methodology could be used against a hypoactive immune system in AD. Two cytokines that play a role in brain cognitive function (GCSF and GMCSF) are often much reduced in blood of AD subjects. By increasing blood levels of these cytokines to normal or above normal levels, electromagnetic fields may indirectly induce beneficial changes to cognitive areas of the brain. Accordingly, normalizing (block 203) cytokine levels in blood may include enhancing secretion of GCSF and GMSCF cytokines from circulating white blood cells. This may be done by applying electromagnetic fields to a subject via electromagnetic emitters (FIG. 1, 102).

Doing so may impact certain brain components. That is, increasing (block 203) cytokine levels back to normal from being below normal may include increasing the number of microglial (immune) cells in the brain, increasing synapses (connections) in the brain, and increasing the number of neurons (neurogenesis) in the hippocampus. Thus, by elevating abnormally low GCSF and GMCSF levels in blood, electromagnetic fields indirectly induce physical changes to the brain that benefit cognitive function. Although TEMT reduced the higher than normal baseline levels of GCSF and GMCSF present in some AD subjects, the reductions were typically to normal or near normal levels typical of aged non-impaired individuals.

Subjects with a hypoactive immune system, such as AD subjects, would then stand to benefit greatly from TEMT administration through a reactivation or rejuvenation of their immune system to confront AD pathogenesis. Conversely, subjects with one of the many diseases/conditions characterized by a hyperactive immune system, such as the "cytokine storm" of COVID-19, could get relief from this immune hyperactivity through TEMT administration and a resultant lowering of cytokine levels.

Note that among the eight cytokines exhibiting immunoregulation by TEMT, this regulation was universally in the same direction. For example, the AD subjects who had higher than normal levels of these eight cytokines always responded to TEMT with a reduction in levels of all eight cytokines—and vice versa for those having below normal cytokine levels. Thus, the present method (200) provides a generalized immunoregulation toward normal levels irrespective of whether a given cytokine is pro- or anti-inflammatory. This is a unique immunoregulatory response not exhibited by any other technology or drug.

In yet another example of addressing imbalance in blood levels of various cytokines, the method (200) may be performed on a body of a user using a peripheral electromagnetic treatment (PEMT) device employing an electromagnetic wave generator (FIG. 1, 108), and cable-connected electromagnetic emitters (FIG. 1, 102) to generate and radiate electromagnetic field treatment into the body of the subject beneath the electromagnetic emitter(s) (FIG. 1, 102). In one specific example, there may be one or multiple electromagnetic emitters (FIG. 1, 102) depending on the disease/condition to be treated. As an example, a subject with serious COVID-19 infection may require multiple electromagnetic emitters (FIG. 1, 102) positioned bilaterally on the neck, axial arm region, and lower chest in order to suppress the cytokine storm and lower lung inflammation typical of serious COVID-19 infections. In this example, the neck and axial emitters would affect major blood and lymphatic vessels in those body regions to lower the high blood cytokine levels of the patient's cytokine storm while the lower lung emitters would concurrently lessen the high lung cytokine levels causing lung inflammation in the COVID-19 infected patient.

In all the above examples and many more applications of either TEMT or PEMT to meet addressing imbalance in blood levels of various cytokines, the following ranges of electromagnetic wave parameters being emitted may be used:
a. an electromagnetic wave frequency of 1 MHz to 430 GHz
b. a power level of 0.1 to 8 W/kg average Specific Absorption Rate (SAR)
c. a pulse repetition rate of 1 to 300 Hz
d. a duty cycle between 1% and 100% (continuous).

Accordingly, the present specification describes a method of applying electromagnetic fields to alter cytokine levels in a subject possibly by directly activating or suppressing cytokine release from immune cells (e.g., lymphocytes, conventional T (Tcon) cells, macrophages, and mast cells). Such a method may also activate or suppress Treg cells which would then modulate cytokine release from immune cells.

Figure 3:
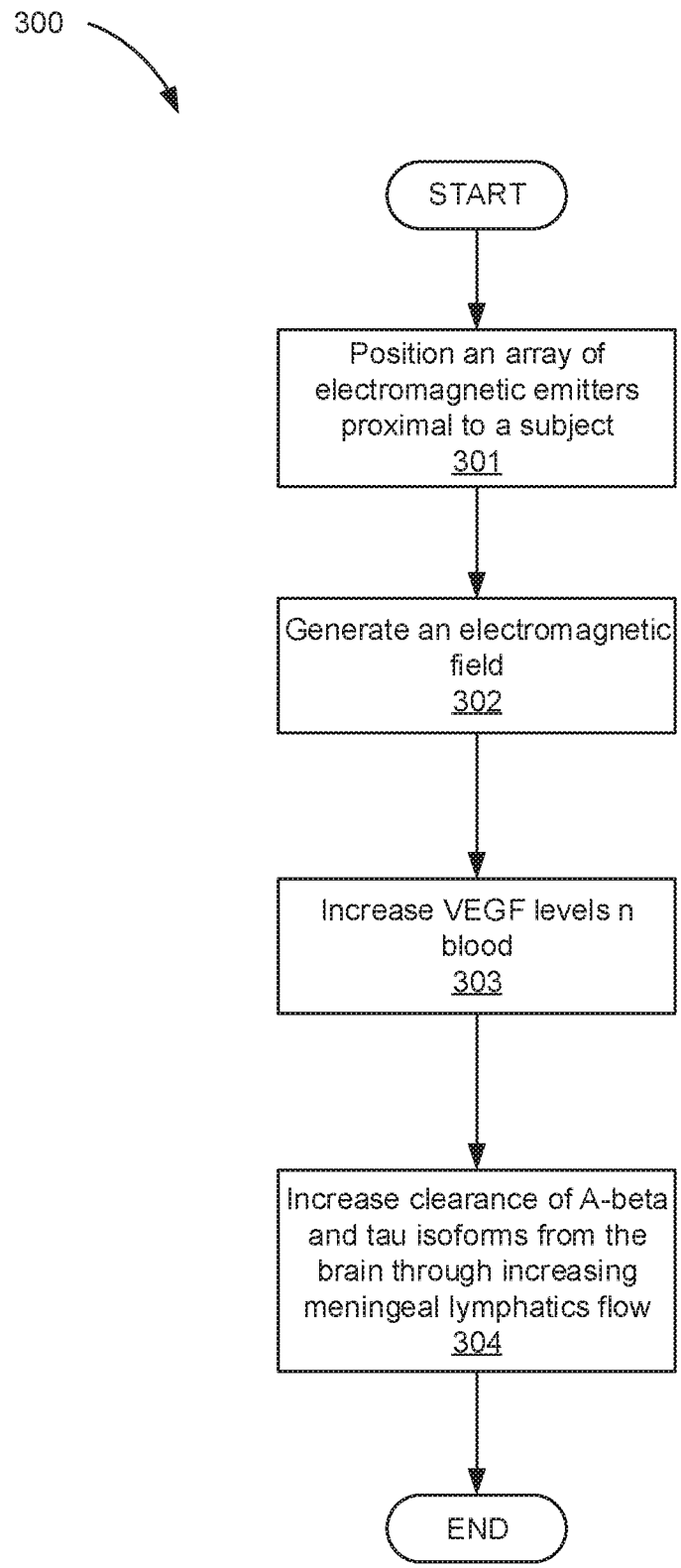
FIG. 3 is a flowchart of a method for normalizing cytokine levels in a blood stream of a subject, according to another example of the principles described herein.

FIG. 3 is a flowchart of a method (300) for normalizing or enhancing cytokine levels in a blood stream of a subject, according to another example of the principles described herein. As described above, the method (300) may include positioning (block 301) an array of electromagnetic emitters (FIG. 1, 102) proximal to a subject and generating (block 302) an electromagnetic field, that then results in emission of electromagnetic fields from electromagnetic emitters (FIG. 1, 102).

The method may also include increasing (block 303) VEGF levels in the blood. Vascular Endothelial Growth Factor (VEGF) is a cytokine that aides in development and adulthood maintenance of meningeal lymphatic vessels. Studies have shown that increased levels of VEGF in blood directly enhance the size (diameter) of meningeal lymphatics, which may result in greater lymph flow through these dilated vessels. Accordingly, increasing blood levels of the cytokine VEGF may "indirectly" increase lymph flow through the meningeal vessels by inducing dilation of meningeal vessels.

In AD subjects having low blood VEGF levels, a single 1-hour TEMT session results in large increases in blood VEGF levels. After 60 days of TEMT in the same AD subjects, the increase in blood VEGF levels is even larger. These results are consistent with TEMT-induced higher VEGF levels in blood indirectly increasing meningeal lymphatic flow, which would enhance clearance of toxic proteins (e.g., Aβ and tau) from the brain.

Accordingly, increasing (block 303) blood VEGF levels may be equally as well employed by use of a body or peripheral electromagnetic treatment (PEMT) device. The same or different electromagnetic emitters (FIG. 1, 102) could be positioned on the body surface to generate electromagnetic waves, resulting in projection of ensuing electromagnetic field treatment into the body of the subject beneath the electromagnetic emitter(s) (FIG. 1, 102), such as on the neck and axial regions to impact the large vascular and lymphatic vessels in these body regions. There may be one or multiple electromagnetic emitters (FIG. 1, 102) depending on the disease/condition requiring treatment.

Electromagnetic wave-induced secretion of VEGF from circulating blood cells (e.g., lymphocytes, mast cells) via a TEMT device or a PEMT device increases meningeal lymphatic flow and consequently enhances toxic protein removal from the brain by this pathway.

In this example, the method (300) may also enhance removal of toxic proteins from the brain. Specifically, the method (300) may include increasing (block 304) a clearance of β-amyloid (Aβ) and tau isoforms, along with other brain toxins and metabolites from the brain through increasing meningeal lymphatics flow. That is, two toxic proteins that are the root cause of AD, namely β-amyloid (Aβ) and tau, may have increased clearance from the brain through this method. According to the method (300), these isoforms are continually removed from the brain so that they do not build up into self-aggregating toxic "oligomers" or insoluble deposits. Indeed, a dysfunction in clearance of these two proteins has been hypothesized to be a major reason for why their oligomeric and insoluble forms build up in the AD brain. Until recently, it was assumed that the only route to clear Aβ and tau from the brain was via transport through the cerebrospinal fluid (CSF) and then into the venous blood. However, it has been determined that the brain includes an extensive system of "meningeal" lymphatic vessels that are present on the brain surface within dura membranes. These lymphatic vessels drain the brain's fluid into cervical lymph nodes, which then drain the lymph into large veins to thus clear various toxins from the brain. As such, these meningeal lymphatic vessels and their one-way lymph flow to the venous system represents a second route for toxic protein clearance from the brain. Therefore, the method (300) which increases (block 304) Aβ and tau clearance from the brain through meningeal lymphatic vessels would be highly desirable.

Accordingly, the electromagnetic fields emanating from the various electromagnetic emitters (FIG. 1, 102) on the head surface, as exemplified and described above, may directly affect the brain's meningeal lymphatic vessels as well as the lymphocytes within them. The electromagnetic waves from brain surface emitters may "indirectly" act to enhance drainage/flow into meningeal lymphatic vessels from the brain, resulting in enhanced clearance of toxins out of the brain. This facilitates removal of Aβ and tau from the brain.

In view of the above, increasing (block 304) clearance of Aβ and tau isoforms, along with other brain toxins and metabolites, can be done by applying electromagnetic fields, through TEMT to the human head or through PEMT to the human body, by electromagnetic emitters (FIG. 1, 102) positioned on either the head or body surface, respectively.

Doing so increases removal of toxins (e.g., Aβ, tau) from the brain via enhanced meningeal lymphatic flow/drainage.

In the above example and other applications of either TEMT or PEMT to clear Aβ and tau isoforms, along with other brain toxins and metabolites, the following ranges of electromagnetic wave parameters being emitted are possible:

a. an electromagnetic wave frequency of 1 MHz to 430 GHz
b. a power level of 0.1 to 8 W/kg average Specific Absorption Rate (SAR)
c. a pulse repetition rate of 1 to 300 Hz
d. a duty cycle between 1% and 100% (continuous)

Figure 4:
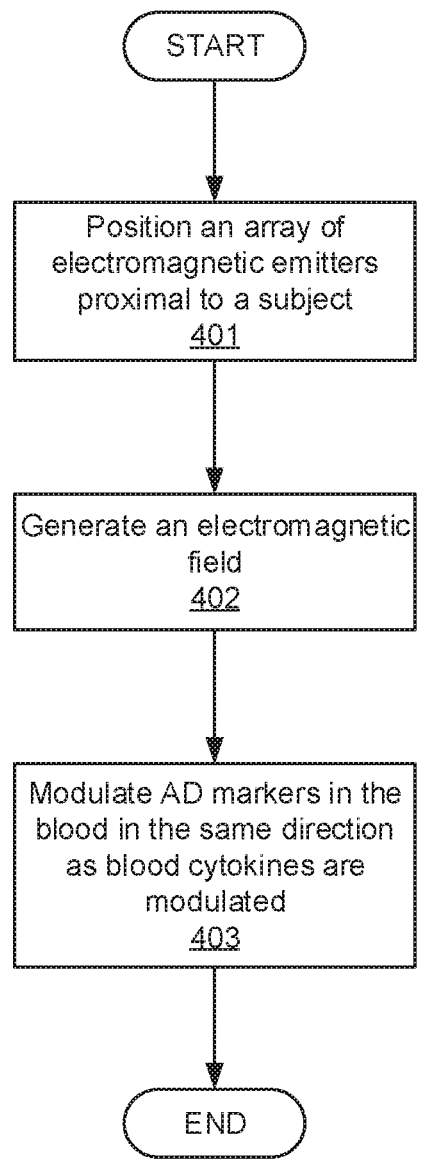
FIG. 4 is a flowchart of a method for modulating AD markers in a blood stream of a subject, according to an example of the principles described herein.

FIG. 4 is a flowchart of a method (400) for modulating AD markers in a blood stream of a subject, according to an example of the principles described herein. As described above, in this method (400), an array of electromagnetic emitters (FIG. 1, 102) are positioned (block 401) proximal to a subject and an electromagnetic field is generated (block 402). This may be done as described above in connection with FIG. 3.

According to the method (400), AD markers in the blood may be modulated (block 403) in the same direction as blood cytokines by applying electromagnetic waves through the electromagnetic emitters (FIG. 1, 102). Specifically, the present specification also describes a method to modulate blood levels of AD markers (e.g., t-tau, p-tau, Aβ1-40, Aβ1-42, oligomeric Aβ) and cytokines such that they are changed in the same direction. For example, it may be desirable for a therapeutic that increased blood cytokine levels induced by the previously described method (300) to induce (directly or indirectly) a higher level of total tau (t-tau) in the blood (the vast majority of which is in the innocuous monomeric tau form). Alternatively, it is equally possible that a methodology-induced increase in blood t-tau then induces increases in certain cytokines in the blood. Of course, both changes in AD markers and cytokines induced by this methodology may occur independent of one another. Thus, a methodology that can regulate blood levels of cytokines and AD markers in the same direction could be of value to protect against or treat AD or other brain diseases/disorders.

In view of the above, modulation of AD markers in the blood may be performed by applying TEMT to the human head or PEMT to the human body through electromagnetic emitters (FIG. 1, 102) positioned on either the head or body surface, respectively. Modulation (block 403) of the AD markers in blood (e.g., t-tau, Aβ1-42) may be in the same direction as changing to blood cytokine levels.

In the above examples and other applications of either TEMT or PEMT methodology to modulate (block 403) AD markers in the blood may be performed by applying, the following ranges of electromagnetic wave parameters being emitted are possible:
a. an electromagnetic wave frequency of 1 MHz to 430 GHz
b. a power level of 0.1 to 8 W/kg average Specific Absorption Rate (SAR)
c. a pulse repetition rate of 1 to 300 Hz
d. a duty cycle between 1% and 100% (continuous)

In some examples, an induced change in an AD marker in the blood indicates a change in blood levels of a cytokine. In another example, an induced change in a blood cytokine level indicates a change in blood levels of an AD marker. In yet another example, an induced change in a blood AD marker occurs independently of a change in blood levels of a cytokine.

Figure 5:
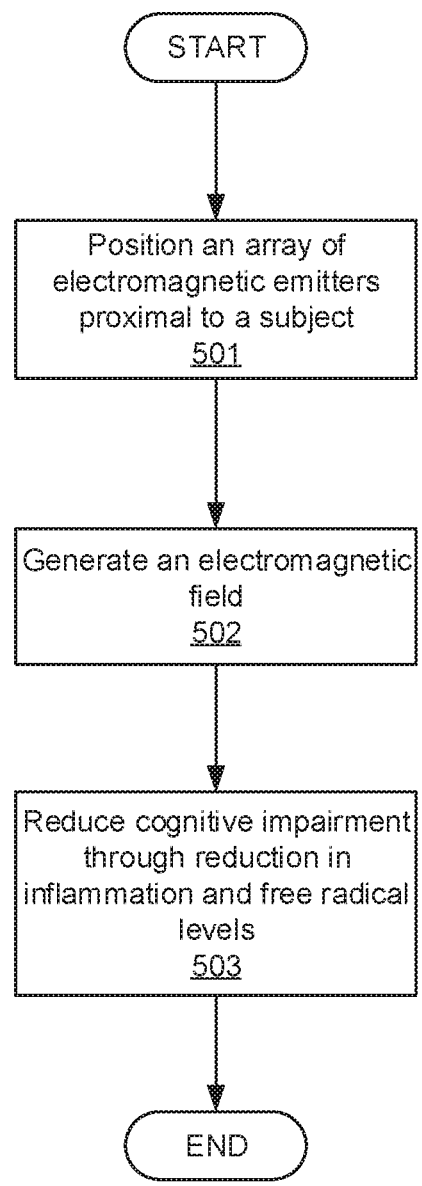
FIG. 5 is a flowchart of a method for treating cognitive impairment via electromagnetic treatment, according to an example of the principles described herein.

FIG. 5 is a flowchart of a method (500) for treating brain fog/cognitive impairment via electromagnetic treatment, according to an example of the principles described herein. As described above, the method (500) includes positioning (block 501) an array of electromagnetic emitters (FIG. 1, 102) proximal to a subject and generating (block 502) an electromagnetic field. According to this method (500), cognitive impairment is reduced (block 503) through reduction in inflammation and free radical levels by applying electromagnetic waves through the electromagnetic emitters to generate electromagnetic fields (FIG. 1, 102).

Such cognitive impairment/brain fog may result from any number of circumstances. For example, the method (500) may prevent or treat the cognitive impairment/brain fog that may occur after a subject has been on artificial ventilation and/or high oxygen for an extended period (such as with serious COVID-19 viral infections) or operating room use of general anesthesia with or without use of a heart-lung machine. That is, viral and bacterial infections can induce a rapid and potent increase in a number of cytokines in the blood, resulting in high fever and lung complications such as inflammation, pneumonia, and fibrosis. These circumstances, such as with COVID-19, may require hospitalization and ensuing ICU attention, the latter of which usually involves artificial ventilation with high oxygen due to difficulty breathing and low blood oxygen saturation. Unfortunately, artificial ventilation may cause an increase in pro-inflammatory cytokines in blood if the lungs are over-inflated. High oxygen (>50%) has also been shown to induce brain fog/cognitive impairment afterwards and can precipitate Alzheimer's Disease—most likely through generation of oxygen free radicals.

In view of the above, cognitive impairment reduction may be met by a method (500) whereby application of TEMT to the human head or PEMT to the human body through electromagnetic emitters (FIG. 1, 102) positioned on either the head or body surface, respectively, can be employed either during or following artificial ventilation and/or oxygen treatment to minimize or eliminate the cognitive impairment that can follow such treatments.

The present method (500) also decreases or eliminates the cognitive dysfunction/brain fog/migraines that may occur following surgery, general anesthesia, and/or in post-perfusion syndrome. That is, it may be that both surgery and anesthesia have long-term effects on cognition at various time points after operations—thus the terms "postoperative cognitive dysfunction" (FOOD). POCD is a complication after surgery with anesthesia in patients 65 years or older and involves both memory impairment and decreased mental capacity. Unfortunately, elderly patients with POCD are three times more likely to experience permanent cognitive impairment or AD compared to those without POCD. There is currently no effective therapeutic to treat POCD. Additionally, general anesthesia, particularly in the elderly or those with pre-existing cognitive impairment, can lead to POCD, which can exacerbate underlying cognitive issues and progress to AD. Use of cardiopulmonary bypass during surgery can also lead to post-perfusion syndrome characterized by brain fog, vertigo, and recurrent migraines. There is clinical evidence for a hyper-active immune system following surgery, general anesthesia, and post-perfusion syndrome. For example, the degree of POCD is correlated with cytokine levels in the blood, suggesting involvement of inflammatory cytokines in POCD. Moreover, there is growing evidence for "neuroinflammation" due to microglial activation in POCD.

In the above application of either TEMT or PEMT to reduce or eliminate the postoperative cognitive dysfunction, cognitive impairment/brain fog that often occurs after a subject has been on artificial ventilation and/or high oxygen for an extended period, the following ranges of electromagnetic wave parameters being emitted are possible:
a. an electromagnetic wave frequency of 1 MHz to 430 GHz
b. a power level of 0.1 to 8 W/kg average Specific Absorption Rate (SAR)
c. a pulse repetition rate of 1 to 300 Hz
d. a duty cycle between 1% and 100% (continuous).

Because general surgery, use of anesthetics therein, and use of cardiopulmonary bypass all involve a hyperactive immune system (high blood cytokine levels), this method more specifically may involve a TEMT- or PEMT-induced reduction in levels of blood cytokine levels (e.g., IL-17a, IL-18) through: a) directly activating or suppressing cytokine release from immune cells (e.g., lymphocytes, macrophages, mast cells), or b) activation or suppression of Treg cells, that then modulate cytokine release from immune cells.

Inasmuch as a hyperactive immune system is often seen following surgery, anesthesia, or by-pass surgery, administration of electromagnetic treatment through either of the aforementioned methods could minimize or eliminate the cognitive impairment induced by such treatments. In any of the examples of reducing cognitive impairment, the treatment method may be used during hospitalization or concurrent with, or immediately following ICU experience, before, during or after hospitalization or out-patient care, and may be used days, months, or years following general anesthesia or use of cardiopulmonary bypass.

Figure 6A:
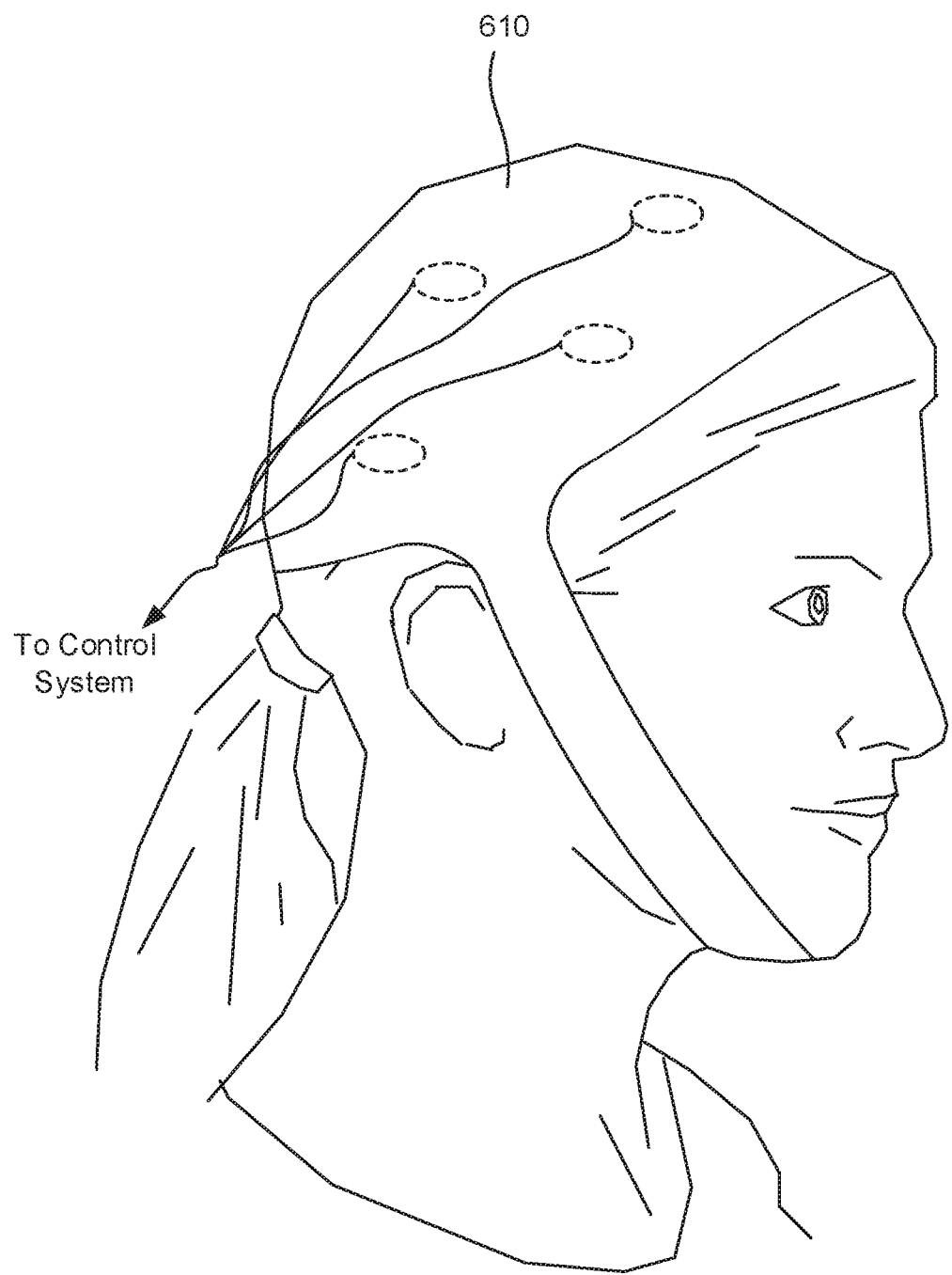
FIGS. 6A-6C depict transcranial electromagnetic treatment (TEMT) to the head, according to an example of the principles described herein.
Figure 6B:
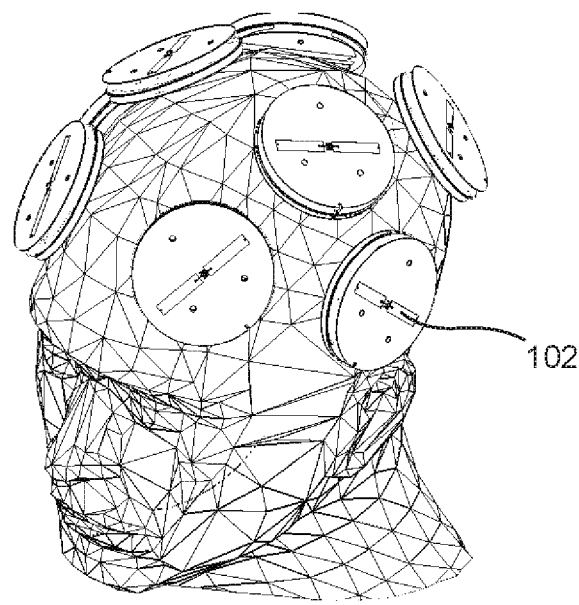
Figure 6C:
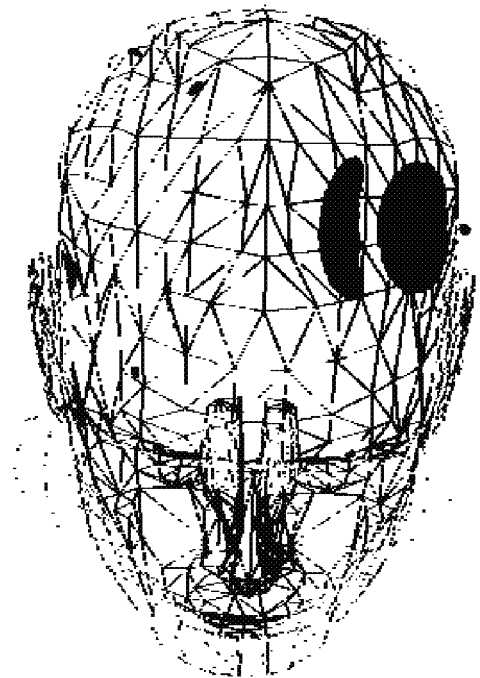

FIG. 6A shows a subject wearing a TEMT device (610), which is an example of a method for providing transcranial electromagnetic treatment (TEMT) to the head. An electromagnetic field is generated by emitters in the head cap through wired connection to a combination control box/battery worn on the arm. A cable containing eight wires connects this control box/battery to each of the eight electromagnetic emitters (FIG. 1, 102) located within a double-layered head cap. The TEMT device (610) allows for near complete mobility in-home, allowing the wearer to perform most home activities while receiving electromagnetic treatment. It can be adjusted to several power levels, and emits no sound. FIG. 6B depicts the size and location of the eight electromagnetic emitters (102) enveloped between the two-layer head cap. For simplicity, a single electromagnetic emitter (102) is indicated with a reference number. Sequential activation of these eight electromagnetic emitters (102) during any given treatment session allows for only one electromagnetic emitter (102) to be active at any given time. FIG. 6C depicts a finite-difference time-domain (FTDT) computer simulation of the electric field generated (dark region of FIG. 6C) by a single active electromagnetic emitter (102) set at 915 MHz frequency and 4.0 W/kg Specific Absorption Rate (SAR). Given the distribution and penetration depth of the electric field from this one active electromagnetic emitter (102) into the brain's temporal lobe, it can be appreciated that all eight electromagnetic emitters (102) during any given treatment collectively provide for full forebrain electromagnetic field treatment. There may be around 200 treatment cycles (emitter activations) per second, but this "pulse repetition rate" can be lower (e.g., 40 Hz) or higher (e.g., 250 Hz).

Figure 7A:
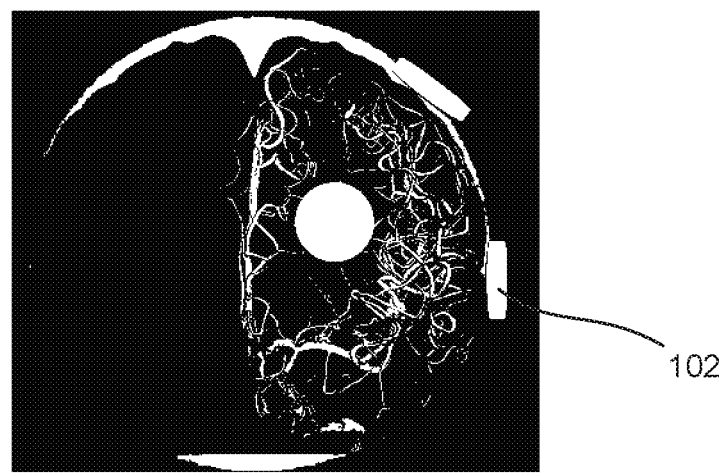
FIG. 7A depicts the arterial vasculature within the human brain and the proximity of those cerebral blood vessels to electromagnetic field emitters positioned on the surface of the head for the example in FIG. 6A.

FIG. 7A depicts the major arterial vasculature within (below the surface of) the human brain and the proximity of those cerebral blood vessels to the electromagnetic emitters (102) of a TEMT device (FIG. 6A, 610). The only barriers between these surface electromagnetic emitters (102) and the surface of the brain are the hair, thin layers of skin and connective tissue, the cranium, and thin layers of dura mater and arachnoid space/pia mater. Given the distribution and penetration of the electromagnetic field emanating from one of the eight electromagnetic emitters (102) (at 915 MHz and 4.0 W/kg), it should be evident that the entire constellation of eight electromagnetic emitters (102) provide electromagnetic treatment to the entire forebrain's deep vasculature in this example.

Figure 7B:
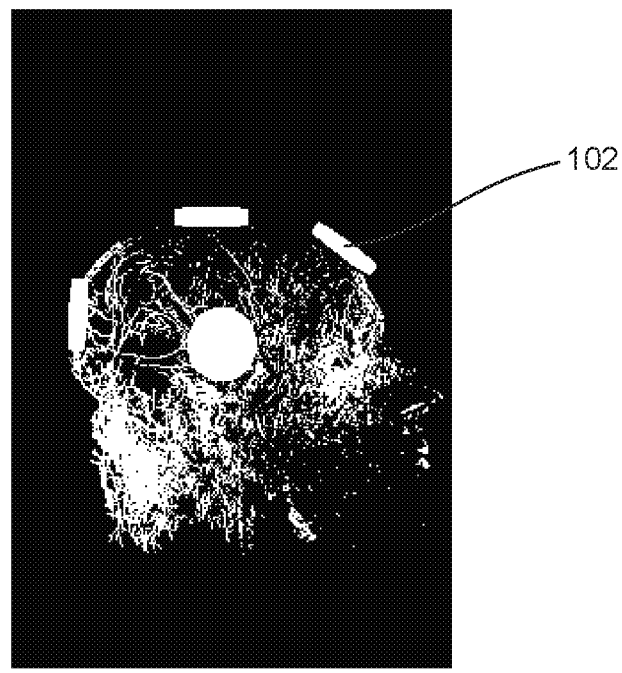
FIG. 7B depicts the arterial vasculature on the surface of the human brain and how emitters for the example in FIG. 6A are also in close proximity to those extra-cranial vessels.

FIG. 7B depicts the dense arterial vasculature on the surface of the human brain and how these vessels are in close proximity to each of the eight electromagnetic emitters (102) of the TEMT device (FIG. 6A, 610) on a human head. In view of the computer-modeled electromagnetic field emanating from each of the eight electromagnetic emitters (102) as depicted in FIG. 6C, it should be evident to one skilled in the art that robust electromagnetic fields bathe both the deep and superficial vasculature of the human brain.

Figure 8A:
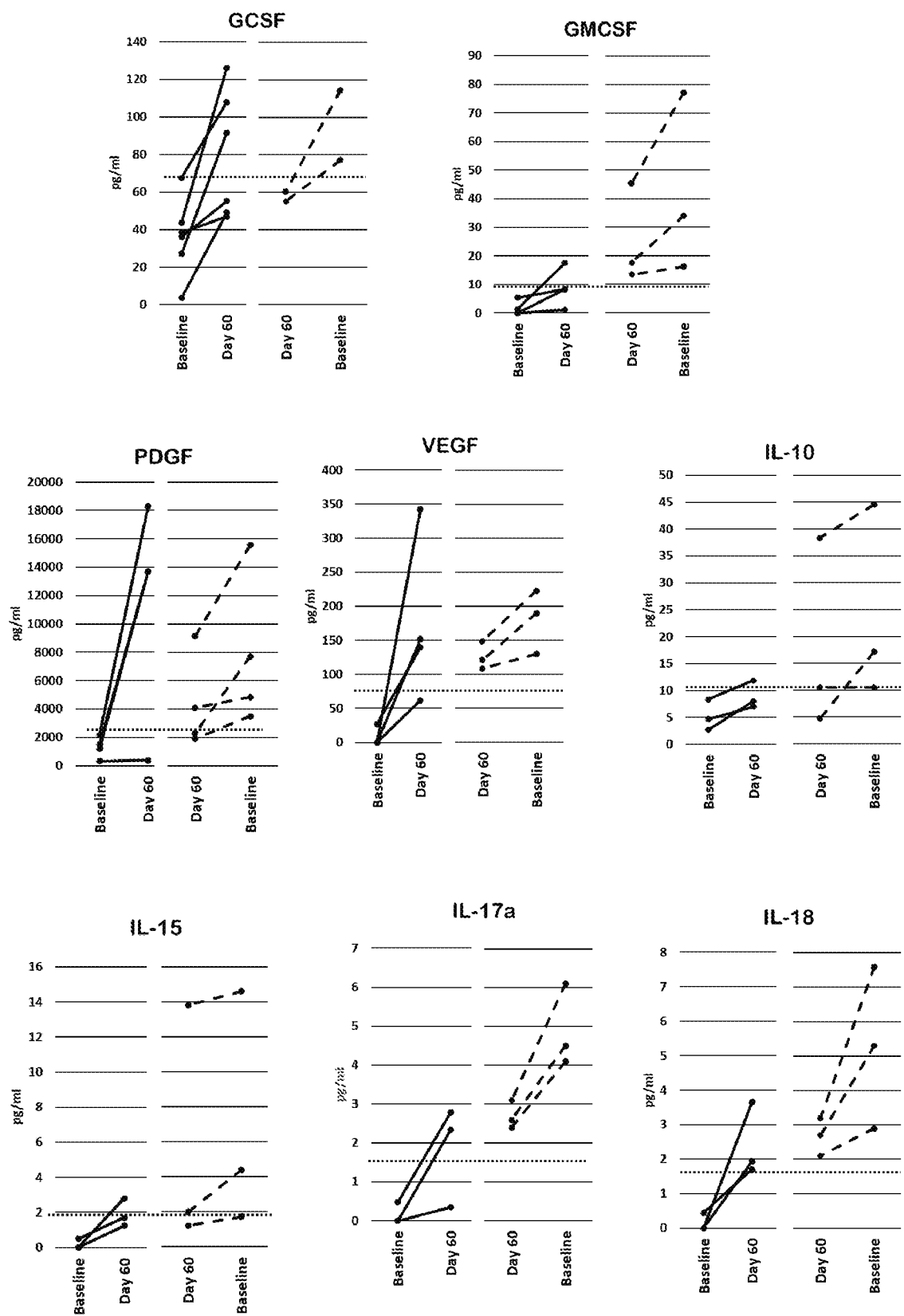
FIG. 8A depicts the effects of 2-months of daily TEMT on blood levels of eight cytokines before (Baseline) and after 2-months of daily TEMT (Day 60) in individual Alzheimer's patients.

FIG. 8A shows graphed results of treating Alzheimer's patients twice daily with the TEMT device (FIG. 6A, 610) on blood levels of eight cytokines. As can be seen for all eight cytokines, if baseline blood levels were abnormally low (below horizontal dotted line for normal levels), TEMT resulted in increased blood levels on Day 60 of treatment (solid lines). Conversely, if baseline cytokine levels were abnormally high, TEMT resulted in decreased blood levels after 60 days of treatment (dashed lines).

In both scenarios, TEMT resulted in plasma cytokine levels being increased or decreased toward or to the mean for aged normal individuals (indicated by dotted horizontal lines). Such information clearly demonstrates that TEMT and the methods described herein provide an "immunoregulatory" role for these eight cytokines by returning their levels to, or closer to, normal and in the case of treating a hypoactive immune system, increasing cytokine levels high above normal levels.

Figure 8B:
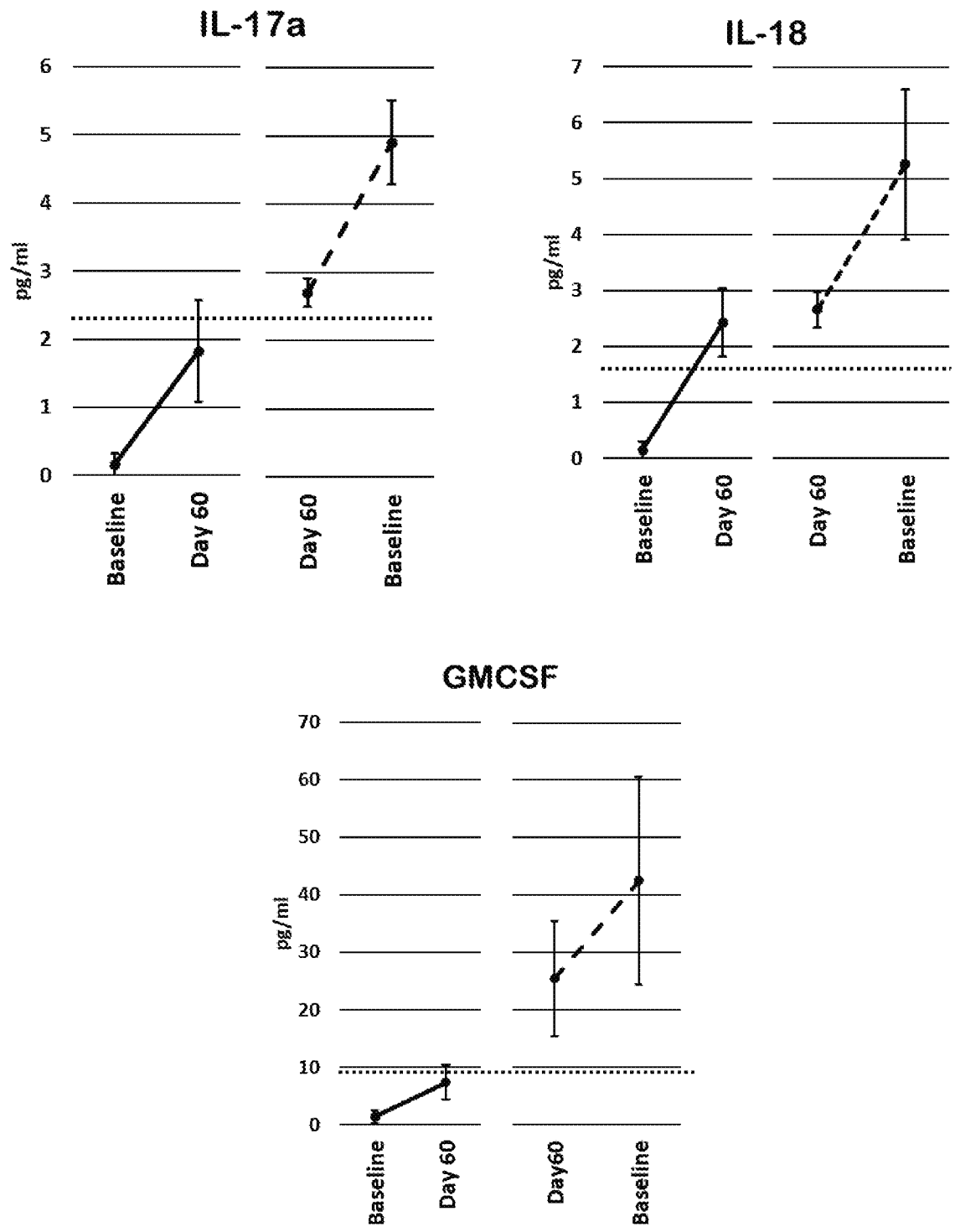
FIG. 8B depicts the effects of 2-months of daily TEMT on blood levels of two of the cytokines shown in FIG. 8A (IL-17a and IL-18), except that means and SEMs are presented for each of the two groups.

The immunoregulatory role of TEMT on blood cytokines is further underscored by FIG. 8B. FIG. 8B depicts means and SEMs for the individual subjects shown in FIG. 8A for IL-17a and IL-18. As is evident, TEMT induced both initially-low and initially-high cytokine groups for both IL-17a and IL-18 to converge toward normal levels for these two cytokines in aged individuals.

Figure 9:
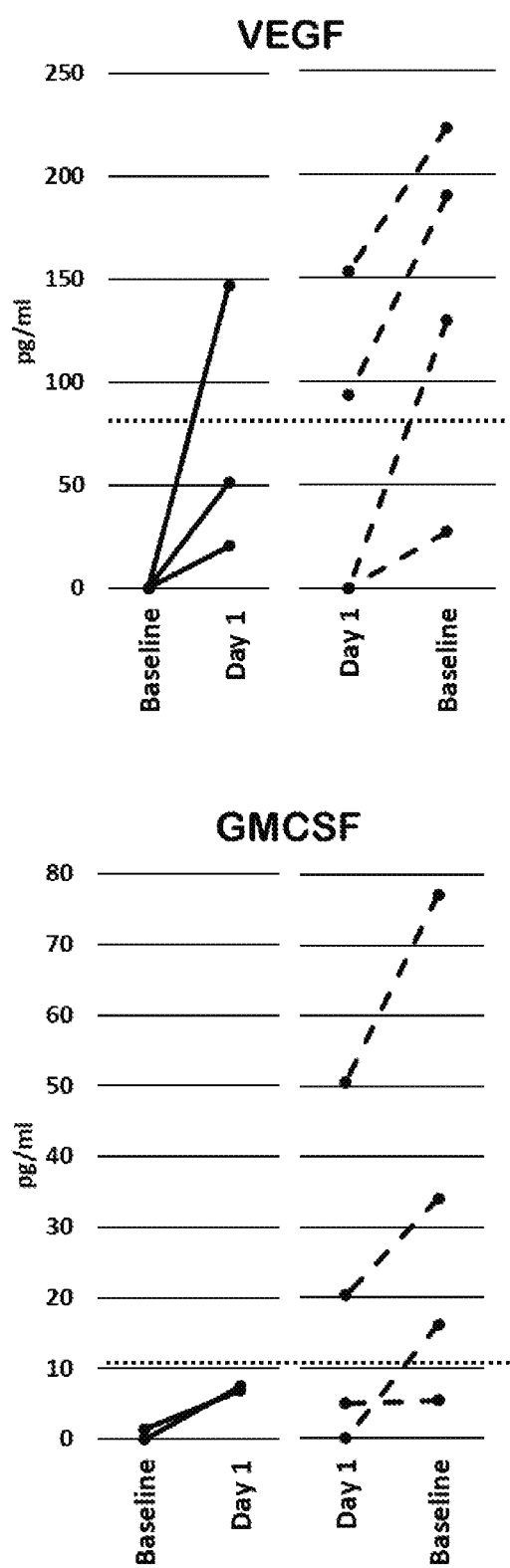
FIG. 9 depicts the effect of a single one-hour TEMT session on blood levels of four cytokines before (Baseline) and after 1-hour of TEMT in Alzheimer's patients.
Figure 9:
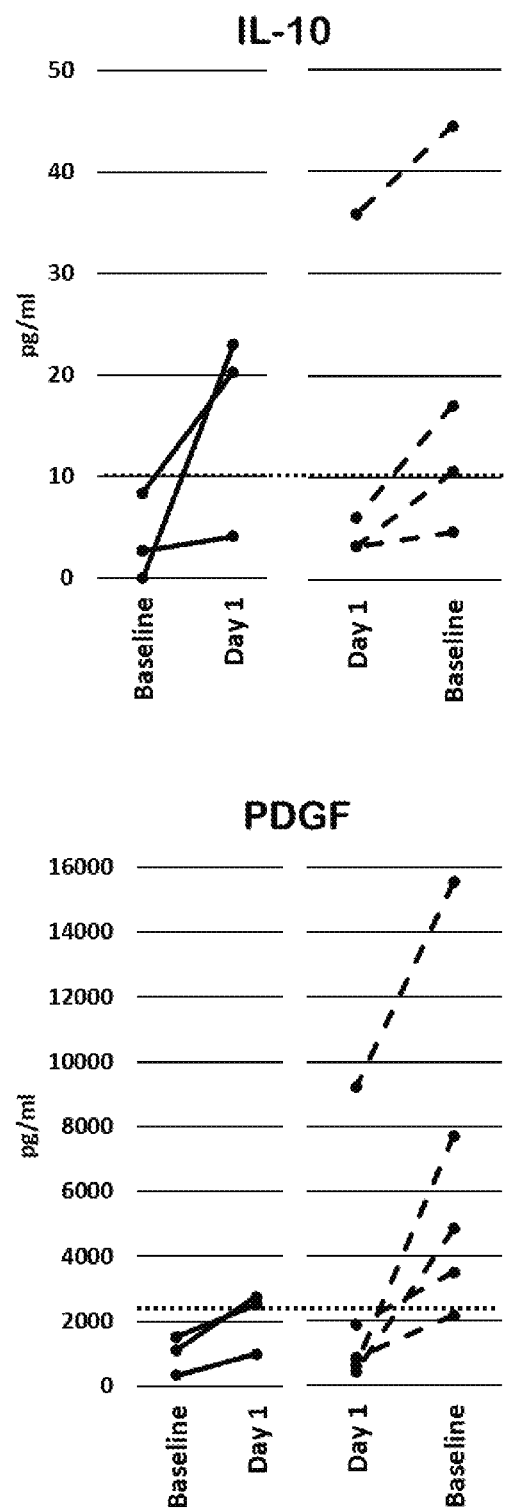

FIG. 9 shows graphed results of treating Alzheimer's patients with the TEMT device (FIG. 6A, 610) on blood levels of four cytokines after only a single one-hour TEMT session. As can be see for all four cytokines, if baseline blood levels were abnormally low (below horizontal dotted line for normal levels), 1-hour of TEMT resulted in increased blood levels shortly thereafter on Day 1 (solid lines). Conversely, if baseline cytokine levels were abnormally high, 1-hour of TEMT resulted in decreased blood levels shortly thereafter on Day 1 (dashed lines).

As was the case for blood cytokines after 60 days of daily TEMT, a consistent profile is seen for all four graphed cytokines (the other four cytokines showed similar results) from the same AD subjects after only a single TEMT session. For AD patients having abnormally low baseline plasma levels (solid lines), a single TEMT session increased their cytokine levels to near, or slightly greater than, normal. For AD patients showing abnormally high baseline levels of these cytokines, a single TEMT session decreased their cytokine levels, often to normal or lower than normal (dashed lines). Therefore, even after only one TEMT session, blood cytokine levels were already trending or reaching normal levels through either an increase or decrease in their levels. As demonstrated in FIG. 9, the methods described herein provide immunoregulatory ability without chronic treatment, but can achieved to a significant degree with acute treatment.

Figure 10:
FIG. 10 shows the human brain's meningeal lymphatic vessels, which appear to remove brain toxins by drainage of their lymph into deep cerebral lymph nodes.

FIG. 10 shows the human brain's meningeal lymphatic vessels, which are largely located on the brain surface within the dura mater. These vessels were recently discovered and are now considered to be a second pathway (in addition to the CSF) for removal/clearance of toxic substances (e.g., Aβ, tau) from the brain. Lymph in these meningeal vessels flows uni-directionally down the neck into the deep cervical lymph nodes, then finally into the large veins feeding into the heart. The meningeal lymphatics have become a target for AD therapeutics since an increase in their lymph flow would remove more toxic Aβ and tau soluble aggregates from the brain. Greater lymph flow in these vessels would presumably enhance clearance of brain toxins.

The cytokine VEGF is a factor that is necessary for the development and maintenance of meningeal lymphatics in adulthood. This cytokine has the ability to dilate meningeal lymphatic vessels to increase their lymph flow. As demonstrated by use of the TEMT device (FIG. 6A, 610) in AD subjects, production/release of VEGF by immune cells (e.g., lymphocytes) in the blood is greatly enhanced in AD subjects having low VEGF levels. Thus, these subjects would be anticipated to have increased meningeal lymphatic flow and resultant increases in brain clearance of Aβ and tau aggregates as a result of TEMT. Indeed, increased levels of soluble Aβ and t-tau are found in plasma of AD patients following 60 days of TEMT.

Figure 11A:
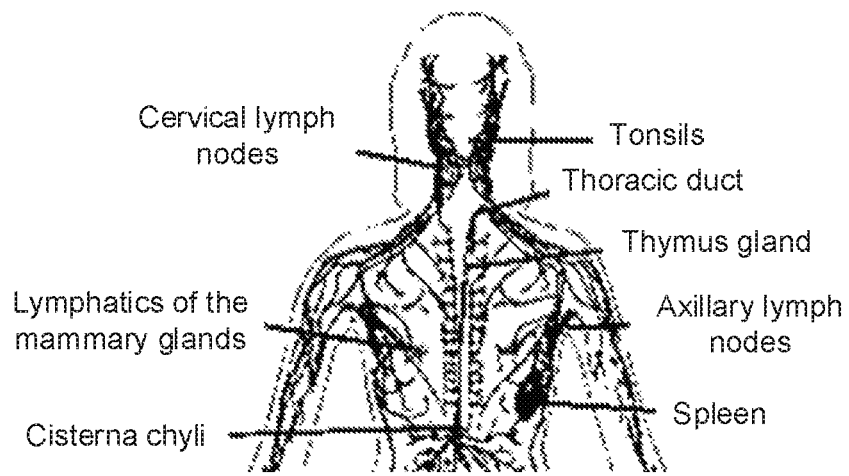
FIG. 11A depicts the lymphatic system within the upper half of the human body.

FIG. 11A shows the lymphatic system within the upper half of the human body. It can be appreciated that lymphatic fluid from the head drains through cervical lymph nodes and that lymphatic fluid returning from the arm and immediate chest region drains through axillary lymph nodes located in the arm's axial region. Lymph from the brain drains through the brain's meningeal lymphatic vessels to deep cervical lymph nodes in the neck, then to large veins that enter the heart. Lymph from the arm and immediate chest region is drained through axillary lymph nodes in the arm's axial region prior to joining the Thoracic Duct.

Figure 11B:
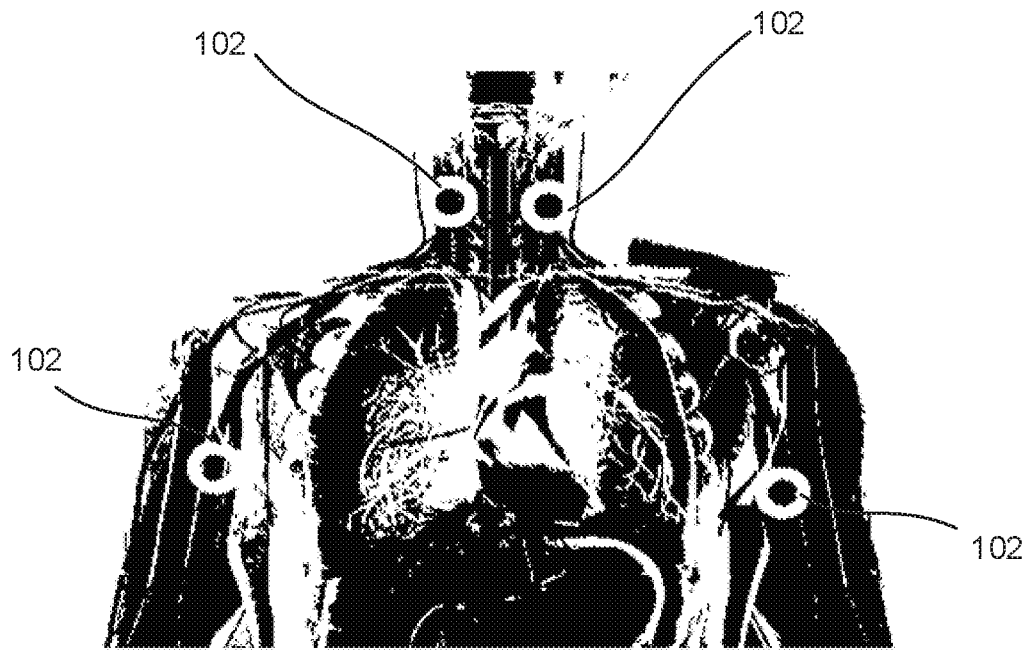
FIG. 11B depicts peripheral electromagnetic treatment (PEMT), specifically with electromagnetic field emitters located above major arterial, venous, and lymphatic vessels in the neck and axial region of the arm.

FIG. 11B shows the major arteries and veins within the upper body. FIG. 11B shows a method for providing peripheral electromagnetic treatment (PEMT), specifically with electromagnetic emitters (102) located above major arterial, venous, and lymphatic vessels in the neck and axial region of the arm. It can be appreciated that WBC's in blood, as well as WBC's in lymph within these major vessels could be readily affected by electromagnetic treatment from these body surface electromagnetic emitters (102).

From FIGS. 11A and 11B, it is clear that two upper body regions contain major arterial, venous, and lymphatic vessels are the neck and axial region of the arm. Thus, if one desired to impact WBCs and their secretion of cytokines, electromagnetic emitters (102) may be placed at these two upper body sites. As such, FIG. 11B shows a method for providing for peripheral (body) electromagnetic treatment (PEMT) with bilateral electromagnetic emitters (102) positioned as indicated located in those two body regions. It can then be appreciated that WBCs (e.g., lymphocytes) in blood, as well as in lymph below these emitters would be most easily and robustly affected.

Figure 12A:
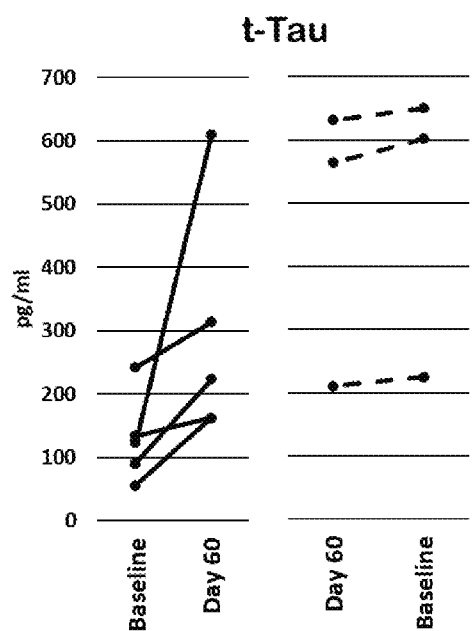
FIG. 12A shows the effects of 60 days of TEMT on blood t-tau levels from individual AD subjects, using the same baseline and Day 60 blood samples from AD subjects that were analyzed for the eight cytokines graphed in FIGS. 8A and 8B.

FIG. 12A depicts graphed results of measuring plasma t-tau levels in the same baseline and Day 60 blood samples from AD subjects as in FIGS. 8A and 8B.

From FIG. 12A, it is clear that the t-tau response of these AD subjects to TEMT has the same general profile as that observed for the cytokines in FIGS. 8A and 8B. This is especially true for the AD subjects having lower blood levels of t-tau at baseline.

Figure 12B:
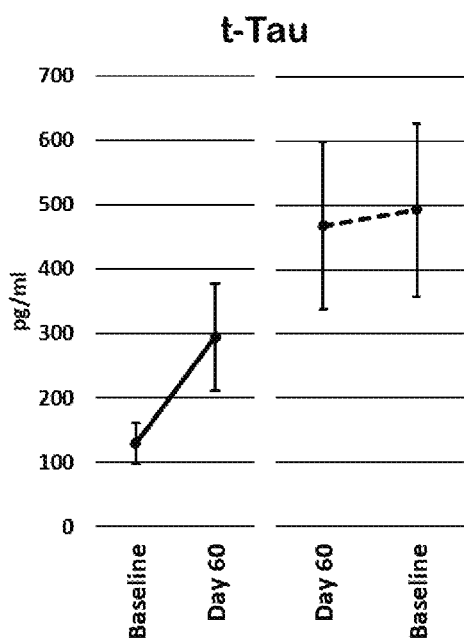
FIG. 12B shows the effects of 60 days of TEMT on blood t-tau levels as the mean±SEM for each of the two groups of AD subjects shown individually in FIG. 12A.

As is readily apparent, the same pattern of TEMT action exhibited by blood cytokines was also present for TEMT actions on blood t-tau levels. With one exception, lower blood levels of t-tau at baseline resulted in increased t-tau levels after TEMT (FIG. 12A; solid lines). Since soluble t-tau is almost totally monomeric tau, this increase may reflect a treatment-induced increase in monomeric t-tau within plasma, which would be consistent with disaggregation of oligomeric tau in plasma. If baseline t-tau levels were higher at baseline, there was a small decrease in t-tau after TEMT (dashed lines). This may be a good effect in keeping soluble (monomeric) t-tau high. FIG. 12B shows the same data as in FIG. 12A, except that means and SEMs of the two groups are presented rather than data from individual subjects. These t-tau results suggest that there is a parallel effect of TEMT on cytokines and t-tau.

The preceding description has been presented only to illustrate and describe the invention. It is not intended to be exhaustive or to limit the invention to any precise form disclosed. Many modifications and variations are possible in light of the above teaching.

The examples described herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. A method of normalizing cytokine levels in a subject, the method comprising:
   positioning an array of electromagnetic wave emitters for transcranial electromagnetic treatment (TEMT) or peripheral electromagnetic treatment (PEMT) proximal to the subject;
   generating, by an electromagnetic wave generator, an electromagnetic field; and
   normalizing cytokine levels in at least one of a blood stream, lymphatic vessels, and brain tissue beneath the electromagnetic wave emitters of the subject by applying the electromagnetic field to the subject through the electromagnetic wave emitters.

2. The method of claim 1, wherein the array of electromagnetic wave emitters is positioned adjacent a head surface of the subject.

3. The method of claim 1, wherein the array of electromagnetic wave emitters is positioned adjacent a body surface of the subject.

4. The method of claim 1, wherein normalizing cytokine levels comprises activating or suppressing cytokine release from at least one of immune cells.

5. The method of claim 1, wherein normalizing cytokine levels comprises increasing cytokine levels when initial cytokine levels are low.

6. The method of claim 5, wherein normalizing cytokine levels comprises increasing cytokine levels for subjects with at least one of Alzheimer's Disease, Acquired Immunodeficiency Syndrome (AIDS), Traumatic Brain Injury (TBI), and chronic widespread pain.

7. The method of claim 1, wherein normalizing cytokine levels comprises decreasing cytokine levels when initial cytokine levels are high.

8. The method of claim 7, wherein normalizing cytokine levels comprises decreasing cytokine levels for subjects with at least one of Alzheimer's Disease, bacterial or viral infections, Rheumatoid Arthritis, Multiple Sclerosis, arterial hypertension, autoimmune diseases, psoriasis, cognitive impairment in depression, allergy, asthma, coeliac disease, glomerulonephritis, hepatitis, inflammatory bowel disease, Crohn's disease, osteoarthritis, fibromyalgia, cardiovascular diseases, cancer, diabetes, chronic obstructive pulmonary disease (COPD), chronic kidney disease, systemic lupus erythematosus, metabolic syndrome, and post-operative cognitive dysfunction.

9. The method of claim 1, wherein normalizing cytokine levels comprises enhancing secretion of granulocyte colony-stimulating factor (GCSF) cytokine and (granulocyte-macrophage colony-stimulating factor (GMCSF) cytokine from circulating white blood cells.

10. The method of claim 1, further comprising at least one of:
    increasing a number of microglial cells;
    increasing synapses in the brain; and
    increasing a number of neurons in a hippocampus.

11. The method of claim 1, wherein the electromagnetic wave emitters are placed over brain glial cells and cerebral vessels.

12. The method of claim 1, wherein the electromagnetic waves of the electromagnetic field have:
    a frequency of 1 megahertz (MHz) to 430 gigahertz ((GHz);
    a power level of 0.1 to 8 watts per kilogram (W/kg) average Specific Absorption Rate (SAR);
    a pulse repetition rate of 1 to 300 hertz (Hz); and
    a duty cycle between 1% and 100%.

13. The method of claim 1, wherein normalizing cytokine levels in the blood stream of the subject by applying electromagnetic treatment to the subject through the electromagnetic wave emitters comprises periodic treatments at predetermined intervals.

14. The method of claim 1, wherein normalizing cytokine levels in the blood stream of the subject by applying electromagnetic treatment to the subject through the electromagnetic wave emitters treats immunological dysfunctions characterized by abnormal blood cytokine levels.

15. The method of claim 1, further comprising enhancing drainage/clearance of amyloid-beta (Aβ) and tau isoforms from the brain, along with other brain toxins and metabolites by applying electromagnetic treatment to the subject through the electromagnetic wave emitters.

16. The method of claim 1, further comprising increasing lymph flow through meningeal vessels by increasing blood levels of vascular endothelial growth factor (VEGF) cytokines to indirectly induce dilation of meningeal vessels.

17. The method of claim 1, further comprising modulating Alzheimer's Disease (AD) markers in blood in the same direction as cytokine levels by applying electromagnetic treatment to the subject through the electromagnetic wave emitters.

18. The method of claim 17, wherein an induced change in an AD marker in the blood indicates a change in blood levels of a cytokine.

19. The method of claim 17, wherein an induced change in a blood cytokine level indicates a change in blood levels of an AD marker.

20. The method of claim 17, wherein an induced change in a blood AD marker occurs independent of a change in blood levels of a cytokine.

21. A method of treating cognitive impairment via electromagnetic treatment, the method comprising:
   positioning at least one electromagnetic wave emitter for transcranial electromagnetic treatment (TEMT) or peripheral electromagnetic treatment (PEMT) proximal to the subject;
   generating, by an electromagnetic wave generator, electromagnetic fields;
   normalizing cytokine levels in a blood stream of the subject by applying electromagnetic treatment to the subject, wherein normalizing cytokine levels comprises activating or suppressing cytokine release from immune cells; and
   reducing cognitive impairment by applying the electromagnetic field to the subject through the at least one electromagnetic wave emitter.

22. The method of claim 21, wherein reducing cognitive impairment comprises treating, by applying electromagnetic treatment to the subject through the at least one electromagnetic wave emitter, at least one of:
   postoperative cognitive dysfunction;
   cognitive impairment following use of a ventilator;
   higher than normal oxygen to the lungs;
   post-perfusion syndrome;
   general anesthetic; and
   use of cardiopulmonary by-pass.

23. The method of claim 21, wherein the at least one electromagnetic wave emitter is positioned adjacent a head surface of the subject.

24. The method of claim 21, wherein the at least one electromagnetic wave emitter is positioned adjacent a body surface of the subject.

25. The method of claim 21, wherein the electromagnetic waves of the electromagnetic fields have:
   a frequency of 1 megahertz (MHz) to 430 gigahertz (GHz);
   a power level of 0.1 to 8 watts per kilogram (W/kg) average Specific Absorption Rate (SAR);
   a pulse repetition rate of 1 to 300 hertz (Hz); and
   a duty cycle between 1% and 100%.

26. A method of normalizing cytokine levels in a blood stream of a subject, the method comprising:
   positioning an array of electromagnetic wave emitters for transcranial electromagnetic treatment (TEMT) proximal to a head of the subject via a headcap;
   generating, by an electromagnetic wave generator, electromagnetic fields, wherein the electromagnetic fields have:
      a frequency of 1 megahertz (MHz) to 430 gigahertz (GHz);
      a power level of 0.1 to 8 watts per kilogram (W/kg) average Specific Absorption Rate (SAR);
      a pulse repetition rate of 1 to 300 hertz (Hz); and
      a duty cycle between 1% and 100%;
   normalizing cytokine levels in the blood stream of the subject by applying electromagnetic treatment to the subject through the electromagnetic wave emitters at predetermined intervals for a predetermined amount of time; and
   enhancing drainage/clearance of amyloid-beta (Aβ) and tau isoforms from the brain, along with other brain toxins and metabolites in response to normalizing cytokine levels.

* * * * *